United States Patent [19]

Lee

[11] Patent Number: 4,957,917

[45] Date of Patent: Sep. 18, 1990

[54] ANTI-INFLAMMATORY FURANONES

[75] Inventor: Gary C. M. Lee, Laguna Hills, Calif.

[73] Assignee: Allergan, Inc., Irvine, Calif.

[21] Appl. No.: 427,201

[22] Filed: Oct. 25, 1989

[51] Int. Cl.$^5$ .................... A61K 31/34; C07D 307/28
[52] U.S. Cl. .................... 514/231.5; 514/255; 514/471; 514/473; 544/152; 544/374; 549/222; 549/313; 549/318
[58] Field of Search .................... 549/318, 313, 222; 514/471, 473, 255, 231.5; 544/152, 374

[56] References Cited

FOREIGN PATENT DOCUMENTS 0209274  1/1987  European Pat. Off. ............ 514/473

Primary Examiner—Glennon H. Hollrah
Assistant Examiner—Amelia A. Owens
Attorney, Agent, or Firm—Martin A. Voet

[57] ABSTRACT

New furanone compounds have anti-inflammatory, immunosuppressive and anti-proliferative activity and are useful in treating psoriasis and modifying calcium homeostasis. A compound of the invention is 4-[1-acetoxy-2-N-(dodecyl) amidoethyl]-5-hydroxy-2(5H)-furanone.

9 Claims, No Drawings

ANTI-INFLAMMATORY FURANONES

This invention relates to new furanone compounds having anti-inflammatory activity, pharmaceutical compositions comprising these compounds and to methods of using them.

BACKGROUND OF THE INVENTION

Manoalide is a furanone compound isolated from marine sponge as reported by E. D. de Silva et al., *Tetrahedron Letters* 21:1611–1614 (1980). Anti-inflammatory, immunosuppressive and analgesic properties of manoalide are disclosed in U.S. Pat. No. 4,447,445. Manoalide has the following structural formula:

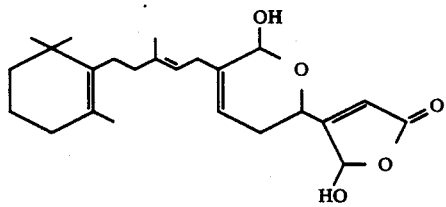

The anti-inflammatory activity of seco-manoalide and dehydro-seco-manoalide is also disclosed in U.S. Pat. No. 4,447,445.

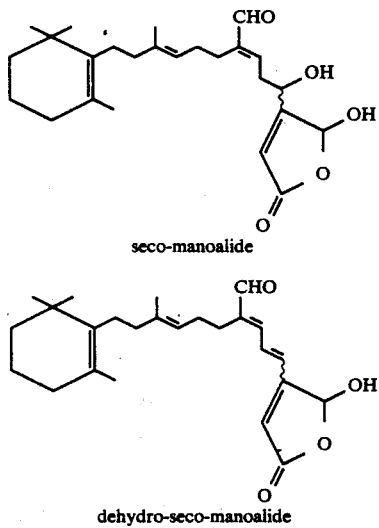

seco-manoalide dehydro-seco-manoalide

SUMMARY OF THE INVENTION

The compounds of the present invention are represented by the following formula:

FORMULA I

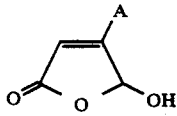

in which:
A is —CH(OCOR$_1$)CH$_2$CO—Y, —CH=C(R$_2$)—R, —CH=CHCO—Z, —CH=C(R$_3$)—CO$_2$R; —C≡CR$_4$, —CH=CH(CH$_2$)$_n$OX or —CH(PH)CH$_2$CO—Y; R is C$_7$–C$_{14}$ alkyl; R$_1$ is C$_1$–C$_4$ alkyl or NHR$_7$; R$_7$ is H, phenyl or C$_1$–C$_4$ alkyl; R$_2$ is halogen or CO$_2$R$_5$; R$_3$ is hydrogen or CO$_2$H; R$_4$ is C$_7$–C$_{14}$ alkyl, phenyl(CH$_2$)$_m$, (CH$_2$)$_n$OX or (CH$_2$)$_n$CO$_2$R$_5$; R$_5$ is C$_1$–C$_4$ alkyl; m is 4–8. n is 7–14; and X is hydrogen, acetyl. PO(OH)$_2$, CO(CH$_2$)$_3$N(R$_1$)$_2$ or CO(CH$_2$)$_3$N(R$_1$)$_2$.HCl or another pharmaceutically acceptable salt; Y is O—C$_7$–C$_{14}$ alkyl or NHR$_6$, Z is C$_7$–C$_{14}$ alkyl, morpholine, N-methylpiperazine or NHR$_6$; and R$_6$ is C$_7$–C$_{14}$ alkyl, phenylethyl, NR$_8$(CH$_2$)$_n$N(R$_9$)$_3$, NR$_8$(CH$_2$)$_n$N(R$_9$)$_3$.HCl or NR$_8$(CH$_2$)$_n$CO$_2$H; R$_8$ is H, C$_1$–C$_3$ alkyl; n is 1–8; and R$_9$ is H or C$_1$–C$_3$ alkyl.

The hydroxy group in the 5-position on the furanone ring may be acylated or alkylated by standard procedures, for example, by reacting the hydroxyfuranone with an acyl anhydride or halide or with an alkyl halide to give compounds also having anti-inflammatory activity as do the 5-hydroxy furanone of Formula I.

Particular compounds of this invention are represented by Formula I in which:
A is —CH(OCOR$_1$)CH$_2$CO$_2$R, —CH=C(R$_3$)—CO$_2$R or —C≡CR$_4$.

A preferred A group is —CH=CH—CO$_2$R.

Specific compounds of this invention are, for example:

4-(2-carbooctanoxy)ethenyl-5-hydroxy-2(5H)-furanone, 4-(1-acetoxy-2-carbooctanoxy)ethyl-5-hydroxy-2(5H)-furanone, or 4-[1-acetoxy-2-N-(o-ctyl)amidoethyl]-5-hydroxy-2(5H)- or 4-[acetoxy-2-N-(-dodecyl)amidoethyl]-5-hydroxy-2(5H)-furanone.furanone or 4-(1-acetoxy-2-N-(dodecyl)amidoethyl]-5-hydroxy-2(5H)-furanone.

The compounds of this invention contain chiral centers and accordingly, may be prepared as enantiomeric or diasteriomeric mixtures or in optically pure form. Unless otherwise specified herein, such preparations are racemates at each chiral center. However, the scope of the invention is not to be considered as limited to these forms but also to encompass the individual optical isomers of the compounds.

Compounds of the invention are prepared from 5-trimethylsilyl(TMS)-3-furaldehyde by procedures which are illustrated hereinbelow and described in more detail in the examples.

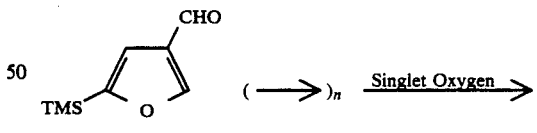

The aldehyde group of 5-trimethylsilyl-3-furaldehyde is converted to the desired A group by one or more steps, n equals at least 1. known to the art or described in the following examples to give the 2-TMS-4-A-furan intermediates. The intermediate is treated with oxygen and irradiated using an initiator such as Rose Bengal to give compounds of the invention.

The 5-trimethylsilyl-3-furaldehyde starting material may be prepared by brominating 3-furaldehye to give 5-bromo-3-furaldehye which is converted to the dimethylacetal, then treated with t-butyl lithium and trimethylsilyl chloride.

A preferred method for preparing 5-trimethylsilyl-3-furaldehyde is by reacting lithium morpholide with 5-bromo-3-furaldehyde to protect the aldehyde group, then reacting with t-butyl lithium and trimethylsilyl chloride to give 5-trimethylsilyl-3-furaldehyde.

An improved method for preparing 5-trimethylsilyl-3-furaldehyde consists of reacting lithium morpholide with 3-furaldehyde, followed by secondary-butyl lithium, followed by trimethylsilyl chloride. This method is also advantageous for the preparation of 5-triethylsilyl-3-furaldehyde using triethylsilyl chloride. 5-Triethylsilyl-3-furaldehyde is useful as an intermediate in place of the trimethyl compound in methods described herein for preparing compounds of this invention.

The pharmaceutically acceptable, nontoxic, acid addition salts having the utility of the free bases of these compounds are formed with inorganic or organic acids, for example maleic, fumaric, benzoic, ascorbic, pamoic, succinic, methanesulfonic, acetic, propionic, tartaric, salicylic, citric, gluconic, aspartic, stearic, palmitic, glycolic, p-aminobenzoic, glutamc, benzenesulfonic, hydrochloric. hydrobromic, sulfuric, cyclohexylsulfamic, phosphoric and nitric acids. This is not intended to be an exhaustive list. Such salts can be prepared by methods well known in the art.

In addition, this invention relates to pharmaceutical compositions containing the compounds of Formula I as active ingredients and to methods of using the compounds and pharmaceutical compositions of this invention to produce anti-inflammatory, immunosuppressant and anti-proliferative activity. These compounds are useful in treating inflammation, in suppressing unwanted immune responses and in retarding proliferation of cells. Other uses include treatment of rheumatoid arthritis, osteoarthritis, rheumatic carditis and autoimmune diseases such as allergic diseases, bronchial asthma and myasthenia gravis and ocular and dermal inflammatory diseases. The compounds are useful in treating psoriasis, acne, atopic diseases and allergic conjunctivitis. They are also useful as adjuvant therapy associated with organ and tissue transplants.

The activity of the compounds of this invention is demonstrated by inhibition of the enzyme phospholipase $A_2$ in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide and may indicate anti-inflammatory utility. Bennett et al, *Molecular Pharmacology* 32:587–593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells. $GH_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula I and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05–5% of the active ingredient.

A typical cream formulation may contain the following:

| Ingredient | Parts by Weight |
| --- | --- |
| Water/glycol mixture (15% or more glycol) | 50–99 |
| Fatty alcohol | 1–20 |
| Non-ionic surfactant | 0–10 |
| Mineral oil | 0–10 |
| Typical pharmaceutical adjuvants | 0–5 |
| Active ingredients | 0.05–5 |

A typical ointment formulation may contain the following:

| Ingredients | Parts by Weight |
| --- | --- |
| White petrolatum | 40–94 |
| Mineral Oil | 5–20 |
| Glycol solvent | 1–15 |
| Surfacant | 0–10 |
| Stabilizer | 0–10 |
| Active Ingredient | 0.05–5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40–99 |
| Magnesium stearate | 1–2 |
| Cornstarch | 10–20 |
| Active ingredient | 0.001–20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The following examples are intended to illustrate the invention but are not limiting. All temperatures are in degrees Centigrade. NMR data are recorded in delta ppm.

Preparation of Intermediate

5-Trimethylsilyl-3-furaldehyde n-Butyl lithium (a 1.6 M solution in hexane; 31.0 ml, 49.7 mmol) was added dropwise to a solution of morpholine (4.33 ml, 49.7 mmol; freshly distilled from barium oxide) in tetrahydrofuran at −78° under argon. After 15 minutes, a solution of 5-bromo-3-furaldehyde (7.5 g, 49.7 mmol) in tetrahydrofuran was added dropwise. Stirring was continued for 30 min. and n-butyl lithium (a 1.6 M solution in hexane; 46.6 ml, 74.5 mmol) was added dropwise. After 1 hour at −78°, chlorotrimethylsilane (18.9 ml, 149 mmol) was added and stirring continued while the cooling bath attained room temperature. The reaction mixture was quenched with 10% hydrochloric acid and the phases were separated. The aqueous phase was stirred, in the presence of ethyl ether (30 ml), with 10% hydrochloric acid at 0° C. for ½ hour. The organic phases were combined, washed (brine), dried (magnesium sulfate) and evaporated down. The residue was distilled under vacuum to give the title aldehyde as a colorless oil b.p. 48°–50°/0.25 torr.

$^1$H NMR(CDCl$_3$): 0.29(5.9H), 6.98(5.1H), 8.25(5.14) and 9.95 (5.1H).

$^{13}$C NMR (CDCl$_3$): −2.0, 116.2, 128.9, 155.3, 164.1 and 184.5.

MS m/e: Exact mass calculated for C$_8$H$_{12}$O$_2$Si 168.0607, found 168.0588.

Alternative Preparation of Intermediate

5-Trimethylsilyl-3-furaldehyde

N-Butyl lithium (a 2.5 M solution in hexane; 28.8 ml, 72 mmol) was added to a solution of morpholine (6.28 ml, 72 mmol) in tetrahydrofuran (700 ml) at −78° under argon. After 20 minutes. 3-furaldehyde (7.0 g, 72 mmol) was added. After another 20 minutes, sec-butyl lithium (a 1.3 M solution in cyclohexane; 55.4 ml, 72 mmol) was added dropwise and stirring continued at −78° for 7 hours before trimethylsilyl chloride (27 ml, 21.6 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated down to give a light brown oil, which was purified by flash chromatography on silica using 2% ethyl ether/hexane. Fractions with R$_f$ of about 0.30 (silica, 10% ethyl ether/hexane) on evaporation gave the title aldehyde as a light yellow oil, b.p. 48°–50°/0.25 torr.

$^1$H NMR (CDCl$_3$): 0.29 (s, 9H), 6.98 (s, 1H), 8.25 (s, 1H) and 9.95 (s, 1H).

$^{13}$C NMR (CDCl$_3$): −2.0. 116.2, 128.9, 155.3, 164.1 and 184.5.

EXAMPLE 1

Octyl 1-acetoxy-3-(5-trimethylsilyl-3-furyl)propionate

Octyl acetate (235 mg, 1.37 mmol) was added dropwise to a solution of lithium diisopropylamide (1.37 mmol) in tetrahydrofuran (10 ml) at −78° under argon. After 25 minutes, a solution of 5-trimethylsilyl-3-furaldehyde (210 mg, 1.24 mmol) in tetrahydrofuran 92 ml) was added, followed by acetic anhydride (0.35 ml, 3.73 mmol) after 1½ hours. Stirring was continued overnight (16 hours) while the cooling bath attained room temperature. The mixture was quenched with water and extracted with ethyl ether. Evaporation of the dried (magnesium sulphate) extract gave an oil, which was flash chromatographed on silica using 10% ethyl ether/petroleum ether. Fractions with R$_f$ of about 0.15 on evaporation afforded the title trimethylsilylfuran as a colorless oil.

$^1$H NMR: (mixture of diasteriomers) (CDCl$_3$) 0.28 (s, 9H), 0.36 (s, 9H), 0.92 (t, 3H, J=6.9 Hz), 1.31 (brs, 10H), 1.63 (brm, 2H), 2.07 (s, 3H), 2.10 (s, 3H), 2.80 (dd, 1H, J=15 Hz. 5.6 Hz), 3.0 (m, 1H), 4.11 (d, 2H, J TM 6.7 Hz), 6.23 (m, 1H), 6.63 (s, 1H), 7.68 (s, 1H) and 7.60 (s, 1H).

MS m/e (% abundance): 400 ((M+NH$_4$)$^+$4), 383 (M$^+$+1, 2), 382 (M$^+$, 7), 340 (100). 323 (88) and 90 (10).

4-(1-Acetoxy-2-carbooctanoxy)ethyl-5-hydroxy-2(5H)-furanone

A mixture of octyl 1-acetoxy-3-(5-trimethylsilyl-3-furyl)propionate (142 mg, 0.37 mmol) and Rose Bengal (5 mg) in tetrahydrofuran (7 ml) was exposed to singlet oxygen for 2 hours at −78°. The residue, after solvent removed, was flash chromatographed on silica using 60% ethyl ether/petroleum ether. Fractions with R$_f$ of about 0.15 on evaporation afforded the 4-(1-acetoxy-2-carbooctanoxy)ethyl-5-hydroxy-2(5H)-furanone as a colorless oil.

$^1$H NMR (CDCl$_3$): 0.92 (t, 3H, J=6.5 Hz), 1.31 (brs, 10H), 1.67 (m, 2H), 3.30 (m, 2H), 4.15 (t, 2H, J=6.8 Hz), 5.35 (br, 1H), 5.89 (brt, 1H), 6.10 (s, 1H), 6.17 (s, 1H) and 6.25 (s, 1H).

$^{13}$C NMR (CDCl$_3$): 14.0, 20.6, 20.7, 22.6, 25.8, 28.4, 29.1, 31.7, 37.9, 38.0, 65.7, 65.8, 66.0, 98.0, 119.7, 119.9, 165.0, 169.2, 169.8, 170.1 and 170.3.

MS m/e: exact mass calculated for C$_{17}$H$_{30}$NO$_7$ (M+NH$_4$)$^+$360.2022, found 360.2015.

EXAMPLE 2

Octyl 3-(5-trimethylsilyl-3-furyl)propen-2-oate

Lithium diisopropylamide (a 1.5 M solution in cyclohexane; 1.34 ml, 2.0 mmol) was added dropwise to a solution of octyl acetate (322.2 mg, 193 mmol) in tetrahydrofuran (7 ml) at −78° under argon. After 20 minutes, a solution of 5-trimethylsilyl-3-furaldehyde (324 mg, 1.93 mmol) in tetrahydrofuran (1 ml) was added. Stirring was continued at −78° C. for 1 hour and trifluoromethanesulfonic anhydride (0.65 ml, 3.86 mmol) was added. After 1 hour, 1,8-diazobicyclo[5.4.0]-undec-7-ene (0.58 ml, 3.86 mmol) was added and stirring was continued overnight while the cooling bath attained room temperature. The mixture was diluted with ether (30 ml) and acidified with diluted HCl. Extraction (ethyl ether), washing of the extracts (brine), drying (magnesium sulphate) and evaporation afforded an oil, which was subjected to flash chromatography (silica). Elution with 10% ethyl ether/hexane gave octyl 3-(5-trimethylsilyl-3-furyl) propen-2-oate as a light yellow oil.

$^1$H NMR (CDCl$_3$): 0.29 (s, 9H). 0.91 (t, 3H, J=6.9 Hz), 1.30 (brs, 10H), 1.70 (m, 2H), 4.18 (t, 2H, J=6.8 Hz), 6.17 (d, 1H, J=15.0 Hz), 6.80 (s, 1H), 7.60 (d, 1H, J=15.6 Hz), and 7.84 (s, 1H).

MS m/e (% abundance): 323 (M$^+$+1, 20), 322 (M$^+$, 47), 307 (15), 210 (36), 195 (61), 166 (70) and 73 (100).

4-(2-Carbooctanoxy)ethenyl-5-hydroxy-2(5H)-furanone

A mixture of octyl 3-(5-trimethylsilyl-3-furyl) propen-2-oate (78.9 mg, 0.25 mmol) and Rose Bengal (3 mg) in tetrahydrofuran (5 ml) was exposed to singlet oxygen for 100 minutes at −78° C. The residue, after solvent removal, was flash chromatographed on silica using 60% ethyl ether/petroleum ether. The 4-(2-carbooctanoxy)ethenyl-5-hydroxy-2(5H)-furanone was obtained as a pale yellow oil.

$^1$H NMR (CDCl$_3$): 0.92 (t, 3H, J=6.8 Hz), 1.31 (brs, 10H), 1.72 (m, 2H), 4.24 (t, 2H, J=6.5 Hz), 6.32 (s, 1H), 6.36 (s, 1H), 6.61 (d, 1H, J=16.1 Hz) and 7.48 (d, 1H, J=16.1 Hz).

$^{13}$C NMR (CDCl$_3$): 14.1, 22.6. 25.9. 28.6, 29.2, 31.8, 65.8, 97.6, 123.2, 128.8, 132.0, 158.3, 165.8 and 170.0.

MS m/e: exact mass calculated for C$_{15}$H$_{23}$O$_5$ (M+H)$^+$ 283.1545, found 283.1553.

EXAMPLE 3

(E)-1-(2-Trimethylsilyl-4-furyl)-2-carbomethoxy-tridec-1-ene

Potassium bis(trimethylsilyl)amide (a 0.5 M solution in toluene; 14.5 ml, 7.24 mmol) was added to a solution of dodecyltriphenylphosphonium bromide (1.82 g, 3.56 mmol) in tetrahydrofuran (10 ml) at −78° under argon. After one hour, methyl chloroformate (0.28 ml, 3.56 mmol) was added, followed by 5-trimethylsilyl-3-furaldehyde (300 mg, 1.78 mmol) after one hour. Stirring was continued overnight while the cooling bath attained room temperature. The mixture was quenched with methanol/water (30 ml, 1:1). Extraction (ethyl ether/hexane, 1:1) and evaporation of the dried (magnesium sulfate) extracts gave an oil, which was flash chromatographed on silica using 20% ethyl ether/hexane. The title ester was obtained as a pale yellow oil.

$^1$H NMR (CDCl$_3$): 7.8 (s, 1H), 7.5 (s, $^1$H), 6.75 (s, 1H), 3.77 (s, 3H), 3.65 (s, 1H), 2.5 (t, J=7.5 Hz, 2H), 2.3 (q, J=7.5, 2H), 1.3 (m,18H), 0.87 (t. 7.5 Hz, 3H).

$^{13}$C NMR(CDCl$_3$): −1.8, 14.1, 22.6, 28.1, 28.6, 29.2, 29.3, 29.4, 29.6, 29.8, 31.8, 51.8, 120.1, 129.0, 131.0, 148.2, 162.1 and 168.9

MS m/e (% abandance): 379 (M$^+$, 100), 363(27), 347(19), 323(54), 275(18), 229(50), 183(23), 105(36) and (17).

4-(2-carbomethoxytridec-1-enyl)-5-hydroxy-2(5H)-furanone A mixture of (E)-1-(2-trimethylsilyl-4-furyl)-2-carbomethoxy-tridec-1-ene (100 mg, 0.26 mmole) and Rose Bengal (10 mg) in acetone (20 ml) was exposed to singlet oxygen at −78° for two hours. The residue, after solvent removal, was purified by preparative thin layer chromatography (TLC) (20×20 cm, 500 μ silica plate; developed with 50% ethyl ether/hexane). The title furanone was obtained as a white solid.

$^1$H NMR (CDCl$_3$): 7.15 (s, 1H), 6.15 (d, J=3.7 Hz, 1H), 6.2 (s, 1H), 3.83 (s, 3H), 2.52 (t, 2H J=7.5 Hz), 1.4 (m, 18H), 0.87 (t, 3H, J=7.5 Hz).

$^{13}$C NMR (CDCl$_3$): 171.1, 167.4, 158.6, 143.8, 125.4, 120.4, 99.2, 52.6, 31.8, 29.8, 29.6, 29.5, 29.3, 28.7, 22.6, 14.1.

MS m/e: exact mass calculated for C$_{19}$H$_{30}$O$_5$ 339.2171 (M$^+$+1), found 339.2166.

EXAMPLE 4

(E)-4-(2-Bromo-1-tridecenyl)-2-trimethylsilylfuran

Potassium bis(trimethylsilyl)amide (a 0.5M solution in toluene; 6 ml, 3.02 mmol) was added dropwise to a solution of dodecyltriphenylphosphonium bromide (761 mg, 1.49 mmol) in tetrahydrofuran (10 ml) at −78° under argon. After 2 hours, a solution of bromine (81 μl, 1.49 mmol) in tetrahydrofuran (1 ml) was added. followed by a solution of 5-trimethylsilyl-3-furaldehyde (250 mg, 1.49 mmol) in tetrahydrofuran (1 ml) after 1 hour. Stirring was continued at room temperature for 2 days and the mixture was poured into methanol/water (30 ml, 1:1). Extraction (ethyl ether/hexane, 1:1) and evaporation of the dried extracts (magnesium sulphate) gave an oil which was chromatographed on silica using 10% ethyl ether/hexane. Fractions with R$_f$ of about 0.71 on evaporation afforded the title alkene as a pale yellow oil.

$^1$H NMR (CDCl$_3$) 0.31 (s, 9H), 0.93 (t, 3H, J=7.0 Hz), 1.31 (brs, 16H), 1.65 (m, 2H), 2.69 (t, 2H, J=7.7 Hz), 6.61 (s, 1H), 6.69 (s, 1H), 7.32 (s, 1H) and 7.63 (s, 1H).

MS m/e (% abundance): 400/398 (M$^+$, 7), 385/383 (1), 319 (27), 277 (4), 263 (10), 247 (20), 179 (20), 147 (12), 123 (12), 121 (12), 107 (27), 97 (32), 95 (28) and 73 (100).

4-(2-Bromo-1-tridecenyl)-5-hydroxy-2(5H)-furanone

A mixture of (E)-4-(2-bromo-1-tridecenyl)-2-trimethylsilylfuran (240 mg, 0.6 mmol) and Rose Bengal (5 mg) in tetrahydrofuran (7 ml) was exposed to singlet oxygen at −78° for 2 hours. The residue, after solvent removal, was purified by preparative TLC (20×20 cm, 1000μ silica plate; developed with 60% ethyl ether/hexane). The title furanone was obtained as a yellow oil.

$^1$H NMR (mixture of diasteriomers) (CDCl$_3$): 0.93 (t, 3H, J=6.7 Hz), 1.31 (brs, 16H), 1.70 (m, 2H), 2.75 (2t, 2H), 4.35 (br, 1H), 4.91 (brs, 1H), 6.14 (brs, 1H), 6.15 (br, 1H) and 6.64 (brs, 1H).

$^{13}$C NMR (CDCl$_3$): 14.1, 22.7, 27.9, 28.0, 28.2, 28.4, 28.7, 28.9, 29.3, 29.4, 29.5, 29.6, 31.9, 37.8, 38.8, 70.5, 98.7, 117.0, 119.9, 121.5, 128.2, 143.6, 144.2, 158.8 and 171.6.

EXAMPLE 5

5-Trimethylsilyl-3-furaldehyde is treated with carbon tetrabromide and triphenylphosphine in dichloromethane at 0° to give 3-(2,2-dibromoethenyl)-5-trimethylsilylfuran. Treating with n-butyl lithium and 5-phenylpentyl iodide and hexamethylphosphoramide gives 3-(7-phenyl-1-heptynyl)-5-trimethylsilylfuran.

A mixture of the above prepared furan compound and Rose Bengal in tetrahydrofuran is exposed to singlet oxygen at −78° for 2 hours to give 4-(7-phenyl-1-heptynyl)-5-hydroxy-2(5H)-furanone.

EXAMPLE 6

3-(2,2-Dibromoethenyl)-5-trimethylsilylfuran, prepared as in Example 5, is treated with N-butyl lithium and 11-iodo-0-t-butyldimethylsilylundecan-1-ol and then with acetic acid to give 3-(13-hydroxy-1-tridecynyl)-5trimethylsilylfuran. Oxidizing by the procedure described in Example 5 gives 4-(13-hydroxy-1-tridecynyl)-5-hydroxy-2(5H)-furanone.

EXAMPLE 7

Treating 3-(13-hydroxy-1-tridecynyl)-5trimethylsilylfuran with acetic anhydride gives the 3-(13-acetoxy-1-tridecynyl) compound. A mixture of this compound and Rose Bengal in tetrahydrofuran is exposed to singlet oxygen at −78° for 2 hours to give 4-(13-acetoxy-1-tridecynyl)-5-hydroxy-2(5H)-furanone.

EXAMPLE 6

3-(13-Hydroxy-1-tridecynyl)-5-trimethylsilylfuran is treated with 2-chloro-2-oxo-1,3,2-dioxaphospholane. The resulting intermediate is hydrolyzed to give the 3-(13-PO(OH)$_2$O-1-tridecynyl) compound which is oxidized by the procedure described in Example 7 to give 4-[13-PO(OH)$_2$O-1-tridecynyl]-5-hydroxy-2(5H)-furanone.

EXAMPLE 9

Reacting 3-(13-hydroxy-1-tridecynyl)-5-trimethylsilylfuran with 4-(diethylamino)butyric acid hydrochloride in the presence of 1,3-dicyclohexylcarbodiimide and 4-dimethylaminopyridine and then oxidizing by the procedure described in Example 7 gives 4-(13-diethylaminobutyryloxy-1-tridecynyl)-5-hydroxy-2(5H)-furanone.

EXAMPLE 10

Oxidizing 3-(13-hydroxy-1-tridecynyl)-5-trimethylsilylfuran using Jones reagent (chromic acid) gives the 3-(13-carboxy-1-tridecynyl) compound which is mixed with Rose Bengal and exposed to singlet oxygen at −78° for 2 hours to give 4-(13-carboxy-1-tridecynyl)-5-hydroxy-2(5H)-furanone.

EXAMPLE 11

5-Trimethylsilyl-3-furaldehyde is reacted with dioctyl malonate in tetrahydrofuran in the presence of sodium hydride to give 3-[2,2-di(carbooctanoxy)ethenyl]-5-trimethylsilylfuran which is treated with cold aqueous potassium hydroxide to give 3-[(2-carboxy-2-carbooctanoxy)ethenyl]-5-trimethylsilylfuran. Oxidizing by the procedure of Example 7 gives 4-[(2-carboxy-2-carbooctanoxy)ethenyl]-5-hydroxy-2(5H)-furanone.

EXAMPLE 12

N-Acetyl-2-phenylethylamine

Triethylamine (1.26 ml, 9.08 mmol), followed by acetyl chloride (0.64 ml, 9.08 mmol) was added to a solution of 2-phenylethylamine (1.04 ml, 8.25 mmol) in dichloromethane (16 ml) at 0°. After 2 hours, the solution was poured into water and extracted thoroughly with ethyl ether. Evaporation of the dried (magnesium sulfate) extracts gave an oil, which was purified on silica using 80% ethyl acetate/hexane. The title amide was obtained as a colorless solid.

$^1$H NMR (CDCl$_3$): 1.9 (s, 3H), 2.8 (t, 2H, J=7.0 Hz), 3.47 (dt, 2H, J=7 Hz, 6 Hz), 6.05 (brs, 1H) and 7.20 (m, 5H).

$^{13}$C NMR (CDCl$_3$): 23.0, 35.4, 40.6, 126.3, 128.4, 128.5, 138.8 and 170.1.

MS M/e: Exact mass calculated for C$_{10}$H$_{13}$NO (M+) 163.0997, found 163.0993.

3-[1-Hydroxy-2-N-(2-phenylethyl)amidoethyl]-5-tert-butyldimethylsilylfuran

N-Butyl lithium (a 2.5M solution in hexane; 1.28 ml, 3.2 mmol) was added to a solution of diisopropylamine (0.45 ml, 3.2 mmol) in tetrahydrofuran (3 ml) at 0° under argon. After 10 minutes, a solution of N-acetyl-2-phenylethylamine (250 mg, 1.53 mmol) in tetrahydrofuran (1 ml) was added. After another forty-five minutes, a solution of 5-tert-butyldimethylsilyl-3-furaldehyde (320 mg, 1.53 mmol) in tetrahydrofuran (0.5 ml) was added. Stirring continued overnight (15 hours) while the cooling bath attained room temperature. The mixture was quenched with water and after the phases were separated, the aqueous phase was extracted with ethyl ether. The organic phases were combined, dried (magnesium sulfate) and evaporated down to give an oil, which was purified by flash chromatography on silica using 80% ethyl ether/hexane. Fractions with R$_f$ of about 0.48 on evaporation gave the title amide as a pale yellow oil.

$^1$H NMR (CDCl$_3$): 0.20 (s, 6H), 0.90 (s, 9H), 2.50 (m, 2H), 2.80 (t, 2H, J=6.9 Hz), 3.50 (m, 2H), 4.01 (d, 1H, J=0.6 Hz), 5.05 (m, 1H), 5.90 (m, 1H), 6.60 (s, 1H), 7.30 (m, 5H) and 7.55 (s, 1H).

$^{13}$C NMR (CDCl$_3$): 16.7, 26.3, 35.5, 40.5, 43.4, 63.9, 119.3, 126.6, 127.4, 128.7, 138.6, 143.1, 160.0 and 171.8.

MS m/e (% abundance): 373 (M+, 71), 358 (9), 357 (29), 356 (100), 316 (19), 220 (10), 209 (43), 105 (17) and 91 (10).

3-[1-Acetoxy-2-N-(2-phenylethyl)amidoethyl]-5-tert-butyldimethylsilylfuran

A mixture of 3-[1-hydroxy-2-N-(2-phenylethyl)amidoethyl]-5-tert-butyldimethylsilylfuran (290 mg, 77 mmol), acetic anhydride (0.24 ml) and pyridine (2 ml) was stirred at room temperature overnight (14 hours). Most of the solvent was evaporated and the residue was purified by preparative TLC (20×20 cm, 1000μ; ethyl ether).

$^1$H NMR (CDCl$_3$): 0.20 (s, 6H), 0.90 (s, 9H), 1.98 (s, 3H), 2.60 (dd, 1H, J=9.2 Hz, 1.7 Hz), 2.75 (m, 3H), 3.50 (m, 2H), 5.80 (brm, 1H), 6.17 (m, 1H), 6.59 (s, 1H), 7.20 (m, 5H) and 7.61 (s, 1H).

$^{13}$C NMR (CDCl$_3$): 16.6, 21.0, 26.2, 35.4, 40.5, 42.2, 65.5, 119.5, 123.7, 126.5, 128.6, 138.6, 144.4, 160.0, 168.9 and 169.9.

4-[1-Acetoxy-2-N-(2-phenylethyl)amidoethyl]-5-hydroxy-2(5H)-furanone

A mixture of 3-[1-acetoxy-2-N-(2-phenylethyl)amidoethyl]-5-tert-butyldimethylsilylfuran (300 mg, 0.72 mmol) and Rose Bengal (5 mg) in acetone (50 ml) was exposed to singlet oxygen at −78° for 1 hour. The residue, after solvent removal, was purified by preparative TLC (20×20 cm, 1000μ; developed with ether). The title furanone was obtained as a colorless solid.

$^1$H NMR (CDCl$_3$): 2.06 (s, 3H), 2.82 (m, 4H), 3.50 (m, 2H), 5.82 (brs, 1H), 5.93 (s, 1H), 6.11 (s, 1H), 6.60 (brs, 1H), 7.21 (m, 5H) and 7.70 (br, 1H).

$^{13}$C NMR (CDCl$_3$): 14.0, 20.6, 22.5, 31.5, 35.1, 39.5, 40.8, 66.5, 98.2, 119.6, 126.6, 128.6, 138.2, 165.4 and 169.6.

MS m/e: Exact mass calculated for $C_{17}H_{19}NO_6$(M+) 333.1212, found 333.1211.

EXAMPLE 13

3-(13-Hydroxy-1-tridecynyl)-5-trimethylsilylfuran, prepared as in Example 6, is hydrogenated in ethyl acetate using a poisoned palladium catalyst to give 3-(13-hydroxy-1-tridecenyl)-5-trimethylsilylfuran. Oxidizing by the procedure of Example 7 gives 4-(13-hydroxy-1-tridecenyl)-5-hydroxy-2(5H)-furanone.

none.

EXAMPLE 14

5-Triethylsilyl-3-furaldehyde is reacted with diethyl 2-oxotridecylphosphonate and n-butyl lithium to give 5-triethylsilyl-3-(3-oxo-1-tetradecenyl)furan. Oxidizing using Rose Bengal and oxygen gives 4-(3-oxo-1-tetradecenyl)-5-hydroxy-2(5H)-furanone.

EXAMPLE 15

A mixture of methyl(triphenylphosphoranylidene)acetate (994 mg, 2.97 mmol) and 5-trimethylsilyl-3-furaldehyde (384 mg, 2.28 mmol) in tetrahydrofuran (10 ml) was stirred at room temperature for 48 hours. The reaction mixture was evaporated with a minimum amount of silica and the residue was flash chromatographed on silica using 5% ethyl ether/petroleum ether. Fraction with R$_f$ of about 0.16 on evaporation afforded methyl 3-(5-trimethylsilyl-3-furyl)propen-2-oate as a pale yellow oil.

$^1$H NMR (CDCl$_3$): 0.39 (s, 9H), 3.79 (s, 3H), 6.15 (d, 1H, J=15.9 Hz), 6.79 (s, 1H), 7.60 (d, 1H, J=15.9 Hz) and 7.83 (s, 1H).

$^{13}$C NMR (CDCl$_3$): −2.0, 51.3, 116.7, 122.5, 134.9, 148.6, 162.8 and 167.4.

MS m/e: Exact mass calculated for $C_{11}H_{16}O_3Si$ (M+) 224.0868, found 224.0875.

The above prepared ester is hydrolyzed using potassium hydroxide as a catalyst to give 3-(5-trimethylsilyl-3-furyl)propenoic acid. This acid is reacted with decylamine, 1,3-dicyclohexylcarbodiimide and 4-dimethylaminopyridine to give the acid amide. Oxidizing using Rose Bengal and oxygen as described in Example 7 gives 4-[2-(N-decylamido)ethenyl]-5-hydroxy-2(5H)-furanone.

EXAMPLE 16

Using, in the procedure of Example 15, phenethylamine in place of decylamine the product is 4-[2-(N-phenethylamide)ethenyl]-5-hydroxy-2(5H)-furanone.

EXAMPLE 17

3-[1-Hydroxy-2-N-(2-octyl)amidoethyl]-5-t-butyldimethylsilylfuran is prepared by the procedure of Example 12 using N-acetyl-octylamine in place of N-acetyl-2-phenylethylamine. This intermediate is reacted with acetic anhydride according to the procedure of Example 12 to give the 1-acetoxy intermediate which is mixed with Rose Bengal in acetone and exposed to singlet oxygen at −78° for 1 hour to give 4-[1-acetoxy-2-N-(octyl)amidoethyl]-5-hydroxy-2(5H)-furanone.

EXAMPLE 18

5-Trimethylsilyl-3-furaldehyde is treated with lithium diisopropylamide and 2-tetradecanone, followed by acetic anhydride to give 3-(1-acetoxy-3-ketopentadecanyl)-5-trimethylsilylfuran. Oxidation by the method described in Example 1 gives 4-(1-acetoxy-3-ketopentadecanyl)-5-hydroxy-2(5H)-furanone.

EXAMPLE 19

4-[2,2-Dibromo-1-ethenyl]-2-trimethylsilylfuran A solution of 5-trimethylsilyl-3-furaldehyde (1.0 g, 5.95 mmol) in dichloromethane (2 ml) was added to a solution of triphenylphosphine (3.9 g, 14.9 mmol) and carbon tetrabromide (2.46 g, 7.44 mmol) in dichloromethane (15 ml) at 0° under argon. After 1 hour, the mixture was extracted thoroughly with pentane. Evaporation of the pentane extracts gave an oil, which was flash chromatographed on silica using hexane. Fractions with R$_f$ of about 0.52 on evaporation gave the title silylfuran as a yellow oil.

$^1$H NMR(CDCl$_3$): 0.31(5.9H). 6.98(s, 1H). 7.30(s, 1H) and 8.04(s, 1H).

MS m/e (% abundance): 322/324/326 (M+, 32, 63, 33), 307/309/311(50, 100, 52), 252(15), 228/230(6%, 68)), 137/139(40/41) and 73(68),

4-(1-Tetradecenyl)-2-trimethylsilylfuran n-Butyl lithium (a 1.6M solution in hexane) was added dropwise to a solution of 4-(2,2-dibromo-1-ethenyl)-2-trimethylsilylfuran (502.4 mg. 1.6 mmol) in tetrahydrofuran (5 ml) at −78° under argon. After 1 hour, hexamethylphosphoramide (1 ml), followed by dodecyl bromide (0.77 ml, 3.2 mmol) was added. Stirring was continued for 15 hours while the cooling bath attained room temperature. The reaction mixture was quenched with water and extracted with ethyl ether. Evaporation of the dried (magnesium sulphate) extracts gave an oil, which was flash chromatographed on silica using hexane. Fractions with R$_f$ of about 0.29 on evaporation gave the title alkyne as a colorless oil.

$^1$H NMR (CDCl$_3$): 0.3(s,9H). 0.94(t, 3H, J=7.0 Hz). 1.32 (brs. 18H), 1.65 (m, 2H), 2.41(t, 2H, J=7.1 Hz), 6.65 (s.1H) and 7.77 (s.1H).

MS m/e (% abundance): 332 (M+,20), 317(4), 260(5), 220(12), 179(18), 107(15), 73(15) and 73(100).

4-(1-tetradecenyl)-5-hydroxy-2(5H)-furanone

A mixture of 4-(1-tetradecenyl)-2-trimethylsilylfuran (180 mg. 0.56 mmol) and Rose Bengal in tetrahydrofuran (7 ml) was exposed to singlet oxygen for 2 hours at −78°. The residue, after solvent removal, was purified by preparative TLC (20×20 cm, 1000μ silica plate; developed with 40% ethyl ether/hexane). The title furanone was obtained as a yellow oil.

$^1$H NMR(CDCl$_3$): 0.91(t, 3H, J=6.6 Hz), 1.29 (brs, 18H) 1.65 (m, 2H), 2.49 (t, 2H, J=7.3 Hz), 6.04(s,1H) and 6.15(s,1H).

$^{13}$C NMR (CDCl$_3$): 14.1, 20.1, 22.7, 27.9, 28.9, 29.0, 29.3, 29.4, 29.6., 30.1, 31.9, 71.7, 98.8, 110.3, 123.0, 148.6 and 171.7.

MS m/e: exact mass calculated for C$_{18}$H$_{28}$O$_3$ (M+) 292.2038, found 292.2030.

EXAMPLE 20

Dodecyl 1-acetoxy-3-(5-triethylsilyl-3-furyl) propionate

Dodecyl acetate (240 mg, 1.04 mmol) was added dropwise to a solution of lithium diisopropylamide (1.04 mmol) in tetrahydrofuran (25 ml) at −78° under argon. After 1 hour, a solution of 5-triethylsilyl-3-furaldehyde (200 mg, 0.95 mmol) in tetrahydrofuran (2 ml) was added, followed by acetic anhydride (0.31 ml, 2.85 mmol) after 1 hour. Stirring was continued overnight (17 hours) while the cooling bath attained room temperature. The mixture was quenched with water and extracted with ethyl ether. Evaporation of the dried (magnesium sulfate) extract gave an oil, which was purified by preparative TLC (20×20 cm, 1000μ; developed with 15% ethyl acetate/hexane). The title ester was obtained as a pale yellow oil.

$^1$H NMR (CDCl$_3$): 0.75(q, 6H, J=8.0 Hz), 0.88(t, 3H, J=6.5 Hz), 0.97(t, 9H, J=8 Hz), 1.25(m, 18H), 1.56(m,2H), 2.03(s,3H), 2.78(dd,1H, J=8.8 Hz), 2.95 (dd, 1H, J=8.8 Hz), 4.06, (t, 2H, J=6.7 Hz), 6.2(dd, 1H, J=8.8 Hz, 5.4 Hz), 6.6(s,1H) and 7.65(s,1H).

$^{13}$C NMR (CDCl$_3$): 3.1, 7.2, 14.1, 21.1, 22.6, 25.8, 28.4, 28.5, 29.2, 29.3, 29.2, 29.5, 29.6, 40.1, 64.8, 64.9, 65.0, 119.4, 123.5, 144.7, 159.6, and 169.8 and 169.9.

MS m/e (% abundance): 498 (M+NH$_4$)+, 4), 480(10), 438(50), 422(33), 421(100), 313(60), 271(34), 145(33) and 83(27).

4-(1-Acetoxy-2-carbododecanoxy)ethyl-5-hydroxy-2(5H)-furanone

A mixture of dodecyl 1-acetoxy-3-(5-triethylsilyl-3-furyl)-propionate (234.7 mg, 0.49 mmol), water (0.18 ml) and Rose Bengal (ca.5 mg) in tetrahydrofuran (7 ml) was exposed to singlet oxygen for 2 hours at 0°. The residue, after solvent removal was purified by preparative TLC (20×20 cm, 1000μ; developed with 70% ethyl ether/hexane). The title furanone was obtained as a pale yellow oil.

$^1$H NMR (CDCl$_3$): 0.88(t, 3H, J=6.3 Hz), 1.26(m,18H), 1.64(m,2H), 2.16(s,3H), 2.9(m,2H), 4.1(t, 2H, J=6.7 Hz), 4.9(bd, 1H, J=4.8 Hz), 5.1 (bd, 1H, J=8.5 Hz), 5.8(t, 1H, J=6.4 Hz), 6.07 (s,1H), 6.1(bd, 1H, J=9.8 Hz) and 6.2 (bd,1H, J=8.5 Hz).

$^{13}$C NMR (CDCl$_3$): 14.1, 20.6, 22.6, 25.7, 28.4, 29.1, 29.3, 29.4, 29.5, 29.6, 31.8, 37.9, 65.8, 97.9, 119.7, 164.9, 169.7, 170.1 and 170.2.

EXAMPLE 21

Dimethyl-2-oxotridecylphosphonate

To a stirred solution of methyl laurate (1.5 g, 7.0 mmol) in tetrahydrofuran (120 ml) at −78° was added the lithium salt of dimethyl methylphosphonate (0.901 g, 7.26 mmol) generated with n-butyl lithium (5.29 ml of a 1.39 M solution in hexane). The stirring mixture was warmed to room temperature over four hours and partitioned between ethyl ether and 5% aqueous ammonium chloride solution. The organic portion was washed with 5% sodium bicarbonate, water, saturated sodium chloride solution, dried over magnesiuim sulfate, filtered and concentrated to give a colorless oil. Purification by flash chromatography (silica, 80% to 90% ethyl acetate/hexane) gave the desired phosphonate ester.

IR (CHCl$_3$): 2920, 2850, 1710, 1250 cm$^{-1}$.

$^1$H NMR (CDCl$_3$): 3.81 (s, 3H), 3.77 (s, 3H), 3.09 (d, J=22.7 Hz, 2H), 2.61 (t, J=7.3 Hz, 2H), 1.51 to 1.62 (m, 2H), 1.20–1.35 (m, 16H), 0.88 (t, J=6.7 Hz, 3H).

$^{13}$C NMR (CDCl$_3$): 201.9. 52.9, 52.8, 44.1, 42.0, 40.2, 31.8, 29.5, 29.2, 28.9, 28.8, 23.3, 22.5, 14.0.

MS m/e: Exact mass calcualted for C$_{15}$H$_{31}$O$_4$P (M+) 306.1960, found 306.1963.

(E)-3-(3-Ketotetradecen-1-yl)-5-trimethylsilylfuran

A solution of dimethyl-2-oxotridecylphosphonate (984 mg. 3.21 mmol) in tetrahydrofuran (25 ml) was added to a suspension of sodium hydride (78 mg, 3.21 mmol) in tetrahydrofuran (5 ml) at 0° C. (u.c.) under argon. After 30 min, a solution of 5-trimethylsilyl-3-furaldehyde (450 mg. 2.68 mmol) in tetrahydrofuran (15 ml) was added. Stirring was contained overnight while the cooling bath attained room temperature. The reaction mixture was quenched with saturated ammonium chloride and the organic layer separated. Evaporation of the dried (magnesium sulfate) organic layer gave a residue, which was purified by flash chromotography on a silica using 5% ethyl acetate/hexane to give the title compound.

$^1$H NMR (CDCl$_3$):=0.25(s,9H), 0.84(t, J=6.8 Hz), 1.18–1.35(m, 16H), 1.57–1.70(m, 2J), 2.56 (t, 2H, J=7.5 Hz), 6.44 (d, 1H, J=15.9 Hz), 6.77(s,1H), 7.45 (d, 1H, J=16.0Hz) and 7.82(s, 1H).

$^{13}$C NMR (CDCl$_3$): −2.2, 13.8, 22.4, 26.0, 26.5, 27.2, 29.1, 29.2, 29.3, 29.4, 31.4, 31.7, 32.4, 33.3, 34.6, 36.9, 37.3, 44.9, 51.1, 71.9, 99.2, 101.7, 116.4, 119.7, 172.7 and 178.1.

MS m/e: exact mass calculated for (C$_{21}$H$_{36}$O$_2$Si(M+) 348.2485, found 348.2477.

(E)-4-(3-Ketotetadecen-1-yl)-5-hydroxy-2(5H)-furanone

A mixture of (E)-3-(3-ketotetradecylyl)-5-trimethylsilyl furan (206 mg, 0.59 mmol), Rose Bengal (ca 2 mg) and water (0.05 ml was exposed to singlet oxygen at 0° for 2 hours. The residue, after solvent removal, was purified by flash chromatography using 40% ethyl acetate/hexane. The title furanone was obtained was a pale yellow solid, mp 87°–88.5°.

$^1$H NMR(CDCl$_3$): 0.88 (t, 3H, J=6.6 Hz), 1.29(m, 16H), 1.58–1.70(m, 2H), 2.68 (t, 2H, J=7.4 Hz) 5.70 (brs, 1H), 6.34 (S.1H), 6.36(S, 1H), 6.83 (d, 1H, J=16.5 Hz) and 7.33(d, 1H, J=16.3 Hz).

$^{13}$C NMR (CDCl$_3$): 13.8, 22.4, 23.6, 29.2, 29.4, 31.7, 41.3, 97.9, 123.7, 129.7, 135.0, 159.3, 170.9 and 201.2.

MS m/e: exact mass calculated for C$_{18}$H$_{32}$O+N(M+NH$_4$)+326.2331, found 326.2333.

EXAMPLE 22

N-Acetyl-1-dodecylamine

A mixture of 1-dodecylamine (1.049 g, 5.59 mmol), triethylamine (0.86 ml, 6.15 mmol) and acetyl chloride (0.44 ml, 6.15 mmol) in dichloromethane (10 ml) was stirred at room temperature for 3h. The mixture was quenched with water and the organic phase was separated. Evaporation of the dried (magnesium sulfate) organic phase gave a solid, which was recrystallized from hexane to give the titled amide.

¹HNMR (CDCl₃), 0.92(t, 3H, J=6.9 Hz), 1.29 (brs, 16H), 1.52 (brt, 2H), 1.72 (brm, 2H), 2.00 (s, 3H), 3.26 (q, 2H, J=7.2 Hz) and 5.45 (br, 1H).

LRMS (m/e, % abundance) 228 [(M+H)+, 13), 227 (M+, 34), 156(11), 142(12), 114(33), 100(33), 87(21), 86(41), 60(35) and 55(18).

4-[(2-Acetoxy-2-(N-dodecyl)amido]ethyl-2-trimethylsilylfuran

N-acetyl-1-dodecylamine (627.3 mg, 2.76 mmol) was added to a solution of lithium diisopropylamide (5.80 mmol; generated from 0.81 diisopropylamine and 2.30 ml of n-butyl lithium) in tetrahydrofuran (10 ml) at 0° under argon. After 1 h, a solution of 5-triethylsilyl-3-furaldehyde (580 mg, 2.76 mmol) in tetrahydrofuran (1 ml) followed by acetic anhydride (0.78 ml, 8.29 mmol) after 5h was added. Stirring was continued for 14h while the cooling bath attained room temperature. The mixture was quenched with dilute hydrochloric acid and extracted with ethyl ether. Evaporation of the dried (magnesium sulfate) extracts gave an oil, which was purified by a silica column using 60% ethyl ether/hexane to give the titled furan.

¹HNMR(CDCl₃)=0.72(q, 6H J=6.5 Hz), 0.88(t, 3H, J=6.9 Hz), 0.96(t, 9H, J=7.4 Hz), 1.25(brs, 18H), 1.40(m, 2H), 2.05(s, 3H), 2.68(dd, 1H, J=13.6 Hz, 5.6 Hz), 2.76(dd, 1H, J=13.6 Hz, 8.2 Hz), 3.21(q,2H, J=6.0 Hz), 5.55(brt, 1H), 6.19(m, 1H), 6.59(s,1H) and 7.64(s,1H).

FABMS (m/e, % abundance) 502 [(m+Na)+,1), 437(3), 420(6), 209(26), 115(42), 87(100) and 59(66).

HRMS exact mass calculated for C₂₅H₄₅NO₂Si (M+-HOAc) 419.3220, found 419.3215.

4-[1-Acetoxy-2-(N-dodecyl)amido]ethyl-5-hydroxy-2(5H)-furanone

A mixture of 4-[1-acetoxy-2-(-N-dodecyl)amido]ethyl-2-trimethylsilylfuran (119.0 mg, 0.25 mmol), water (2 drops) and Rose Bengal (5 mg) in tetrahydrofuran (6 ml) was exposed to singlet oxygen at 0° for 40 min. The residue, after solvent removal, was purified by preparative silica plates (developed with ethyl acetate) to give the titled furanone.

¹HNMR (CDCl₃): 0.89(t, 3H, J=6.3 Hz), 1.26(brs, 18H), 1.50(m,2H), 2.15(brs, 3H), 2.90(m, 2H), 3.15(m, 2H), 5.90(br, 1H), 6.04(s, 1H), 6.18(s, 1H), 6.50(br,1H) and 7.85(br, 1H).

¹³CNMR (CDCl₃): 13.8, 20.5, 22.4, 26.6, 28.6, 28.7, 29.0, 29.1, 29.4, 3.71, 39.5, 39.9, 40.1, 66.7, 98.3, 119.7. 119.9, 120.0, 120.1, 120.2, 165.8, 169.7, 169.8, 170.0 and 170.3.

HRMS exact mass calculated for C₂₁H₃₆NO₆(M+H)+398.2542, found 398.2550.

EXAMPLE 23

Dodecyl 3-hydroxy-3-(2-triethylsilyl-4-furyl)propionate

A solution of dodecyl acetate (240 mg, 1.04 mmol) in tetrahydrofuran (2 ml) was added to a solution of lithium diisopropylamide (1.04 mmol; =generated from 0.15 ml of diisopropylamine and 0.42 ml n-butyl lithium at −78°) in tetrahydrofuran (10 ml) at −78° under argon. After 1h, a solution of 5-triethylsilyl-3-furaldehyde (200 mg, 0.95 mmol) in tetrahydrofuran (1 ml) was added. Stirring was continued for 15h while the cooling bath attained room temperature. The mixture was quenched with water and was extracted thoroughly with ethyl acetate. Evaporation of the dried (magnesium sulfate) extracts gave an oil which was purified by a silica column using 20% ethyl ether/hexane to give the titled ester.

¹HNMR (CDCl₃): 0.76(q, 6H, J=8.0 Hz), 0.97(t, 9H, J=8.0 Hz), 1.26(m, 16H), 1.60(m, 2H), 2.75(dd, 2H, J=8.0 Hz, 5.0 Hz), 31.9(d, 1H, J=4.3 Hz), 4.12(t, 2H, J=6.7 Hz), 5.11(m, 1H), 6.64(s, 1H) and 7.61(s, 1H).

¹³CNMR (CDCl₃) : 3.1, 7.3, 14.1, 22.7, 25.8, 28.5, 29.2, 29.3, 29.4, 29.5, 29.6, 31.9, 42.0, 63.4, 65.0, 119.2, 127.0, 143.2 and 172.5.

LRMS (m/e, % abundance) 456[(M+NH₄)+, 100], 211(41) and 145(23).

4-(1-Hydroxy-2-carbododecamoxy)ethyl-5-hydroxy-2(5H)-furanone

A mixture of dodecyl 3-hydroxy-3-(2-triethylsilyl-4-furyl)propionate (131.4 mg, 0.3 mmol), water (a few drops) and Rose Bengal (5 mg) in tetrahydrofuran (8 ml) was exposed to singlet oxygen at 0° for 1.5h. The residue, after solvent removal, was purified by preparative silica plates (developed with 60% ethyl ether/hexane) to give the titled furanone.

¹HNMR(CDCl₃): 0.88(t, 3H, J=7.0 Hz), 1.26(m, 18H), 1.66 (m, 2H), 2.79 (br, 1H), 2.93(br, 1H), 4.14(t, 2H, J=6.7 Hz), 4.93(br, 1H), 5.0(br, 1H), 6.13(br, 1H) and 6.22 (br, 1H).

¹³CNMR(CDCl₃): 13.8, 22.4, 25.6, 28.2, 29.0, 29.1, 29.3, 29.4, 31.7, 39.2, 64.4, 65.7, 98.1, 118.6, 169.0, 171.4 and 172.1.

HRMS exact mass calculated for C₁₉H₃₃O₆ (M+H)+357.2277, found 357.2268.

EXAMPLE 24

Reacting N-acetyl-N',-N'-dimethylethylenediamine (prepared from acetyl chloride and N,N-ethylenediamine) with lithium diisopropylamine, followed by 5-triethylsilyl-3-furaldehyde and dodecanoyl chloride gives 4-[1-dodecanoyloxy-2-[N-N',N'-dimethyl]ethylamido]ethyl-2-trimethylsilylfuran. Oxidizing this intermediate with singlet oxygen gives 4-[1-dodecanoyloxy-2 -[N-(N'N'-dimethyl)-ethylamido]ethyl-5-hydroxy-2(5H)-furanone.

EXAMPLE 25

As in example 24, but substituting N-acetyl-N',N'-dimethylethylenediamine with N-acetyl-N-methyl-N', N'-dimethylethylenediamine (prepared from N-methyl-N',N'-dimethylethylenediamine with acetyl chloride) and carry through the reaction sequence to give 4-[1-dodecanoyloxy-2-[N-methyl-N(N',N'-dimethyl)ethylamido]ethyl-5-hydroxy-2(5H)-furanone.

EXAMPLE 26

Reacting N-acetyl-1-dodecylamine with lithium diisopropylamide and 5-triethylsilyl-3-furaldehyde followed by phenyl isocyanate gives 4-[1-N-phenyl-carbamoyl-2-(N-dodecyl)amido]ethyl-5-trimethylsilylfuran. Oxidizing this intermediate with singlet oxygen gives 4-[1-N phenylcarbamoyl-2-(N-dodecyl)amido]ethyl-5-hydroxy-2(5H)-furanone.

EXAMPLE 27

As in example 26, but substituting N-acetyl-1-dodecylamine with dodecyl acetate and carry through the reaction sequence gives 4-(1-N-phenyl-carbamoyl-2-carbododecanoxy)ethyl-5-hydroxy-2(5H)-furanone.

EXAMPLE 28

As in Example 27, but substituting phenyl isocyanate with chlorosulfonyl isocyanate and carry through the reaction sequence to give 4-(1-uredo-2-carbododecanoxy)-ethyl-5-hydroxy-2(5H)-furanone.

EXAMPLE 29

Reacting 1-N-acetyl-20-(-N',N'-dimethyl)decyl diamine (prepare from 1,10-(-N',N'-dimethyl)decyl diamine with acetyl chloride) with lithium diisopropylamide, followed by 5-triethylsilyl-3-furaldehyde and acetic anhydride gives 4-[1-acetoxy-2(N-10-N',N'-dimethyl)aminodecyl)amido]ethyl-2-trimethylsilylfuran. Treatment of this intermediate with excess iodomethane followed by singlet oxygen oxidation gives r-[1-acetoxy-2-(N-10-(N',N',N'-trimethyl)aminodecyl)amido]ethyl-5-hydroxy-2(5H)-furanone.

EXAMPLE 30

Reacting 10-acetamido-1-undecanoic acid (prepare from 11-amino-1-undecanoic acid and acetyl chloride) with lithium diisopropylamide, followed by 5-triethylsilyl-3-furaldehyde and acetic anhydride gives 4[1-acetoxy-2(N-11-carboxydecyl)amido]ethyl-2-trimethylsilylfuran. Oxidizing this intermediate with singlet oxygen gives 4-[1-acetoxy-2-(N-11-carboxydecyl)amido]ethyl-5-hydroxy-2(5H)-furanone.

EXAMPLE 31

Reacting N-acetyl-N'-methyl-piperazine (prepared from N-methylpiperazine and acetyl chloride) with lithium diisopropylamide, followed by 6-triethylsilyl-3-furaldehyde and dodecanoyl chloride gives 4-[1-dodecanoyloxy-2-(N'-methylpiperazyl)amido]ethyl-2-trimethylsilylfuran. Oxidizing this intermediate with singlet oxygen gives 4-[1-dodecanoyloxy-2-[N'-methylpiperazyl)amido]ethyl-5-hydroxy-2(5H)-furanone.

EXAMPLE 32

As in Example 31, but substituting N-acetyl-N'-methylpiperazine with N-acetylmorpholine and carry through the reaction sequence to give 4-(1-dodecanoyloxy-2-morpholinylamido)ethyl-5-hydroxy-2(5H)-furanone.

EXAMPLE 33

The following test procedures may be used to demonstrate activity of the compounds of this invention:

Inhibition of Phospholipase $A_2$

The effect of compounds of this invention on bee venom phospholipase $A_2$ is determined by the following procedure:

a. Bee venom phospholipasae $A_2$ in 10 μM HEPES (pH 7.4) with 1 mM $CaCl_2$ is incubated with vehicle or test agent for 1.0 hour at 41°.
b. 1.36 mM phosphotidylcholine, 2.76 mM Triton X-100 are dispersed in buffer by sonication and then mixed with L-3 phosphatidylcholine, 1-palmitoyl-2-(1-$^{14}$C) palmitoyl for 10 min.
c. Start the reaction by the addition of enzyme (0.495 units/ml).
d. Incubation for 15 sec. at 41°.
e. Reaction is terminated by addition of 2.5 ml of isopropanol: n-heptane: 0.5 M $H_2SO_4$ (40:10:1; v:v:v).
f. 2.0 ml n-heptane and 1.0 ml $H_2O$ added; mixture centrifuged.
g. 2.0 ml n-heptane removed and treated with 200–300 mg of silica gel HR60.
h. Samples centrifuged; 1 ml of n-heptane SN removed and added to 10 ml scintillation fluid.
i. Samples counted on a scintillation counter.

Inhibition of Phosphoinositide-specific Phospholipase C

The effect of compounds of this invention on phosphoinositide-specific phospholipase C may be determined by procedures described by Bennett et al, *Molecular Pharmacology* 32:587–593 (1987).

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., *Clin Pharmacol Ther* (1974) 16:900–904].

Inhibition of Ornithine Decarboxylase (ODC)

Tape-stripping mouse epidermis and TPA are quick and convenient methods of inducing ODC activity. M. Connor and N. Lowe (*Cancer Res.* 43, 5174, 1983; *Brit. J. Dermatol.* 275, 98, 1984) have studied the ability of retinoids to inhibit ODC. Trans-retinoic acid, 13-cis retinoic acid. and etretinate were all active at inhibiting ODC and therapeutically active in humans. Therefore, inhibition of ODC is an in vivo method to demonstrate the potential efficacy of drugs for epidermal hyperproliferation such as psoriasis. Lowe e. al. (*J. Amer. Acad. Dermatol.* 6:697. 1982) have shown that polyamines and ODC are elevated in psoriasis.

In vitro methods have also been useful in determining the anti-hyperproliferative activity of drugs. C. Marcelo and J. Tomich (*J. Invest. Dermatol.* 81, 64s, 1983) have shown that neonatal mouse keratinocyte cultures can be used to identify drugs that inhibit DNA synthesis. More recently, R. Weiss. Eichner. R. and Sunn, T. T, *J. Cell Biol.*, 98:1397–1406, (1984) have shown that epidermal cultures are in fact, a model of epidermal hyperproliferation and therefore a good model for testing drugs that inhibit hyperproliferation.

Calcium Channel (mobilization) inhibition assay.

Polymorphonuclear leukocytes (PMNa), gastric glands, $GH_3$ cells. A431 cells, spleen cells, human keratinocytes corneal cells. etc. were loaded with the $Ca^{2+}$ sensitive fluorescent dye, Fura-2. The appropriate cell type was chosen and the potency and efficacy of the anti-inflammatory furanones on calcium mobilization, calcium channel inhibition quantitated. The methods used for A431 cells listed below are representative of those used for other cells.

A431 cells were detached using a 5–10 min trypsin-EDTA treatment whereas $GH_3$ cells were treated 2 to 5 min with a 1% pancreatin solution. Cells were immediately washed twice in a 20 mM HEPES buffer (pH 7.4) containing 120 mM NaCl, 6 mM KCl, 1 mM $MgSO_4$, 1 mg/ml glucose and 1 mg/ml pyruvate and 1.4 mM calcium (medium A). Approximately $5 \times 10^6$ cells were suspended in medium A and incubated with 4 μM fura- 2-AM for 15 min at 37° C. After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. $[Ca^{2+}]_i$ was calculated using the following formula:

$$[Ca^{2+}]_i = 220 \frac{F - F_{min}}{F_{max} - F}$$

All fluorescence values were measured relative to a EGTA-quenched signal determined as follows: F was the relative fluorescence measurement of the sample. $F_{max}$ was determined by lysing the cells with digitonin (100 Pg/ml) in DMSO. After $F_{max}$ was determined the pH was adjusted to B, with NaOH and $Ca^{2+}$ chelated with 3 mM EGTA to totally quench the fura-2 signal and obtain $F_{min}$.

When quin-2 was used, cells were incubated with 10 μM quin-2 at 37° C. for 1 hr, washed and then used.

What is claimed is:

1. A compound of the formula:

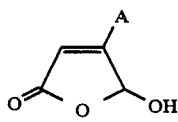

in which:

A is —CH(OCOR$_1$)CH$_2$CO—Y, —CH=C(R$_2$)—R, —CH=CHCO—Z, —CH=C(R$_3$)—CO$_2$R; —C≡CR$_4$, —CH=CH(CH$_2$)$_n$OX or —CH(OH)CH$_2$CO—Y; R is C$_7$-C$_{14}$ alkyl; R$_1$ is C$_1$-C$_4$ alkyl or NHR$_7$; R$_7$ is H, phenyl or C$_1$-C$_4$ alkyl; R$_2$ is halogen or CO$_2$R$_5$; R$_3$ is hydrogen or CO$_2$H ; R$_4$ is C$_7$-C$_{14}$ alkyl, phenyl(CH$_2$)$_m$, (CH$_2$)$_n$OX or (CH$_2$)$_n$CO$_2$R$_5$; R$_5$ is C$_1$-C$_4$ alkyl; m is 4–8; n is 7–14; and X is hydrogen, acetyl, PO(OH)$_2$, CO(CH$_2$)$_3$N(R$_1$)$_2$ or CO(CH$_2$)$_3$N(R$_1$)$_2$.HCl or another pharmaceutically acceptable salt; Y is O—C$_7$-C$_{14}$ alkyl or NHR$_6$; Z is C$_7$-C$_{14}$ alkyl, morpholine, N-methylpiperazine or NHR$_6$; and R$_6$ is C$_7$-C$_{14}$ alkyl, phenylethyl, NR$_8$(CH$_2$)$_n$N(R$_9$)$_3$, NR$_8$(CH$_2$)$_n$N(R$_9$)$_3$.HCl or NR$_8$(CH$_2$)$_n$CO$_2$H; R$_8$ is H, C$_1$-C$_3$ alkyl; n is 1–8; and R$_9$ is H or C$_1$-C$_3$ alkyl.

2. A compound of claim 1 in which A is —CH(OCOR$_1$)CH$_2$CO$_2$R, —CH=C(R$_3$)—CO$_2$R or —C≡CR$_4$.

3. A compound of claim 2 in which A is —CH=CH—CO$_2$R.

4. A compound of claim 1 which is 4-(2-carbooctanoxy)-ethenyl-5-hydroxy-2(5H)-furanone.

5. A compound of claim 1 which is 4-(1-acetoxy-2-carbooctanoxy)ethyl-5-hydroxy-2(5H)-furanone.

6. A compound of claim 1 which is 4-[1-acetoxy-2-N-(octyl)amidoethyl]-5-hydroxy-2(5H)-furanone.

7. A compound of claim 1 which is 4-[1-acetoxy-2-N-(dodecyl)amidoethyl]-5-hydroxy-2(5H)-furanone.

8. A pharmaceutical composition which comprises a pharmaceutical carrier and a therapeutically effective amount of a compound of claim 1.

9. A pharmaceutical composition of claim 8 having anti-inflammatory activity in mammals.

* * * * *